US008894618B2

(12) United States Patent
Smith et al.

(10) Patent No.: US 8,894,618 B2
(45) Date of Patent: *Nov. 25, 2014

(54) PUNCTURABLE MEMBRANE FOR SAFETY SYRINGE

(71) Applicant: Safeshot Technologies, LLC, Mission Viejo, CA (US)

(72) Inventors: Jeffrey Smith, Irvine, CA (US); Daniel Thayer, Mission Viejo, CA (US)

(73) Assignee: Credence Medsystems, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/829,928

(22) Filed: Mar. 14, 2013

(65) Prior Publication Data

US 2013/0204228 A1    Aug. 8, 2013

Related U.S. Application Data

(63) Continuation of application No. 12/544,865, filed on Aug. 20, 2009, now Pat. No. 8,398,601, which is a continuation of application No. 11/982,808, filed on Nov. 5, 2007, now abandoned.

(60) Provisional application No. 60/857,088, filed on Nov. 6, 2006.

(51) Int. Cl.
*A61M 5/32* (2006.01)
*A61M 31/00* (2006.01)
*A61M 5/34* (2006.01)
*A61M 5/31* (2006.01)
*A61M 5/28* (2006.01)

(52) U.S. Cl.
CPC ............. *A61M 5/3134* (2013.01); *A61M 5/347* (2013.01); *A61M 5/288* (2013.01)
USPC .......................................... 604/199; 604/506

(58) Field of Classification Search
CPC .... A61M 5/288; A61M 5/3134; A61M 5/347
USPC .......................... 604/187, 192–199, 240, 506
See application file for complete search history.

(56) References Cited

U.S. PATENT DOCUMENTS 4,973,310 A * 11/1990 Kosinski ....................... 604/110
2006/0129097 A1 * 6/2006 Yang et al. .................... 604/110

* cited by examiner

*Primary Examiner* — Kami A Bosworth
*Assistant Examiner* — Imani Hayman
(74) *Attorney, Agent, or Firm* — K&L Gates LLP

(57) ABSTRACT

A safety syringe may define a variable fluid chamber and detached needle assembly. The variable fluid chamber may be hermetically sealed off from the environment or ambient air until the needle assembly is attached to a syringe body of the safety syringe. A proximal end of the variable fluid chamber is sealed off from the environment via a seal between a piston and syringe body. The distal end of the variable fluid chamber may be sealed off from the environment via a barrier covering the distal end of the syringe body. The barrier may be punctured to allow fluid to through therethrough at or about the same time when the needle assembly is attached to the distal end portion of the syringe body.

17 Claims, 5 Drawing Sheets

PUNCTURABLE MEMBRANE FOR SAFETY SYRINGE

CROSS-REFERENCE TO RELATED APPLICATIONS

This application is a continuation of pending U.S. patent application Ser. No. 12/544,865, filed Aug. 20, 2009 which is a continuation of U.S. patent application Ser. No. 11/982,808, filed Nov. 5, 2007, now issued U.S. Pat. No. 8,398,601, which claims the benefits of U.S. Provisional Patent Application Ser. No. 60/857,088, filed Nov. 6, 2006, the entire contents of which are expressly incorporated herein by reference.

STATEMENT RE: FEDERALLY SPONSORED RESEARCH/DEVELOPMENT

Not Applicable

BACKGROUND

The present invention relates to a safety syringe wherein a variable fluid chamber is hermetically sealed off from contaminated ambient air until a needle assembly is attached to a syringe body such that fluidic medication may be withdrawn from a medication vial and injected into a patient in a sterile manner.

FIG. 1 illustrates a conventional safety syringe with a detached needle assembly. During use, a medical professional may select the appropriate sized needle based on the fluidic medication to be administered to the patient. Once the appropriate sized needle is selected, the needle assembly may be attached to the syringe body of the safety syringe. Unfortunately, a distal end of the syringe body is uncovered. As such, from the time that the syringe is removed from its packaging to the time that the needle assembly is attached to the syringe body, ambient air is allowed to flow into a variable fluid chamber which houses the fluidic medication right before the fluidic medication is injected into the patient. The ambient air flowed into the variable fluid chamber may contain viruses, bacteria or other unwanted contaminants which may be lodged onto the inner surface of the variable fluid chamber. When the fluidic medication is withdrawn into the variable fluid chamber, the contaminant lodged onto the inner surface of the variable fluid chamber may contaminate the fluidic medication to be injected into the patient.

Accordingly, there is a need in the art for a device and a method for injecting fluidic medication into the patient in a sterile manner.

BRIEF SUMMARY

The safety syringe discussed herein addresses the needs discussed above, discussed below and those that are known in the art.

The safety syringe provides a sterile environment in which the fluidic medication may be withdrawn from a medication container and subsequently injected into the patient. More particularly, the safety syringe may have a barrier disposed at a distal end portion of a syringe body of the syringe. The barrier provides an impermeable air barrier between the environment (contaminated ambient air) and the variable fluid chamber. The barrier may be punctured at or about the same time when a needle assembly is attached to the syringe body. When the barrier is punctured, the needle assembly then acts as a cover such that contaminated ambient air does not enter into the variable fluid chamber after the barrier is punctured by the needle assembly. As such, at no time during the process of removing the syringe from its packaging, attaching the needle assembly to the syringe body, withdrawing fluidic medication from a medication container and injecting the patient with the fluidic medication was the variable fluid chamber exposed or allowed to have ambient air flow therein. Hence, the fluidic medication injected into the patient is performed in a sterile manner.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
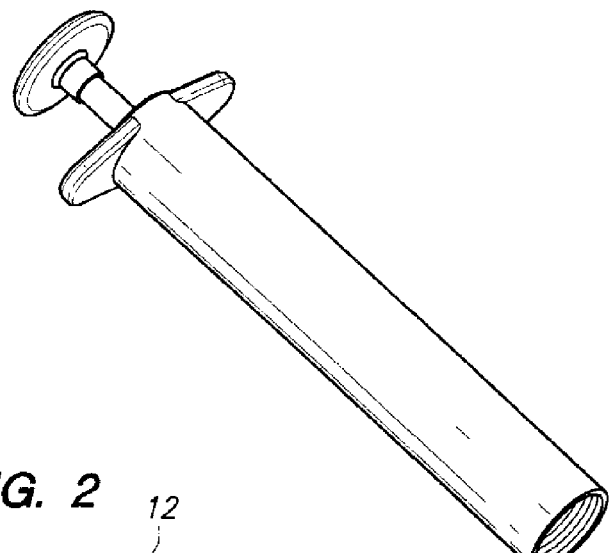
FIG. 1 is a perspective view of a prior art safety syringe.
Figure 2:
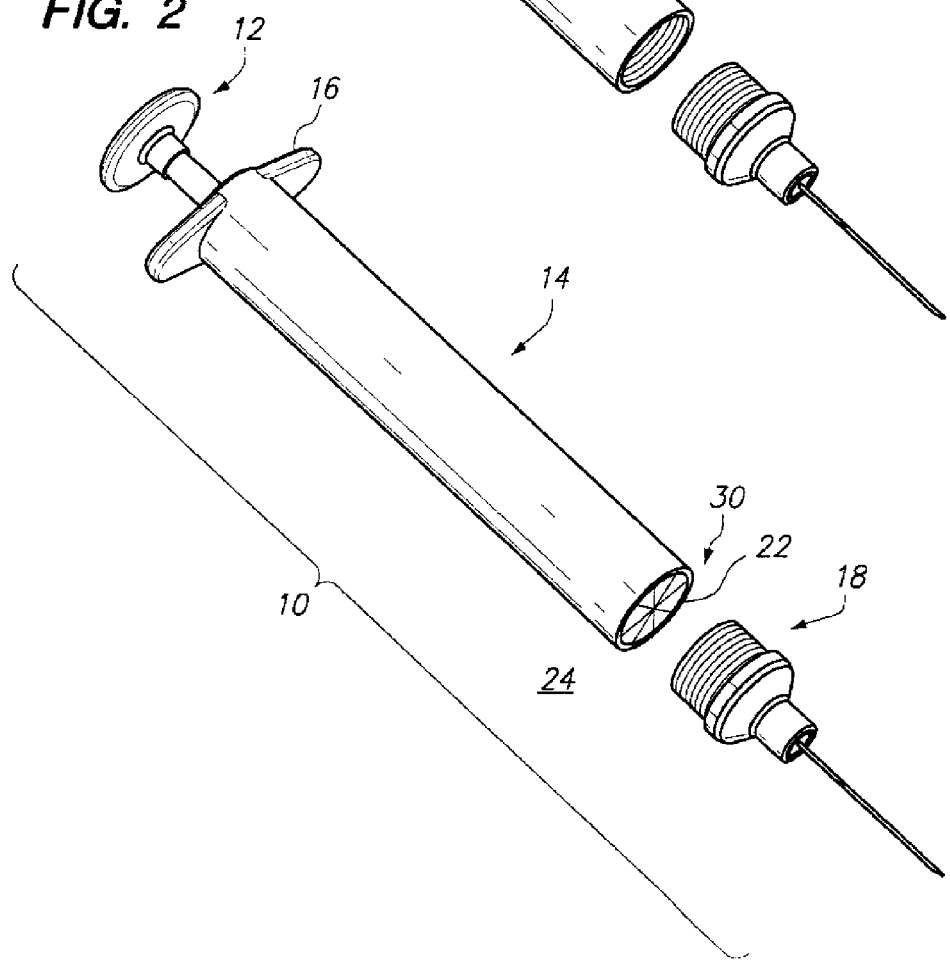
FIG. 2 is a perspective view of a safety syringe with a barrier and a detached needle assembly which is attachable to the syringe body.

Referring now to the drawings, FIG. 2 is a perspective view of a safety syringe 10. In particular, the safety syringe 10 may comprise a plunger assembly 12 partially disposed within a syringe body 14. Finger platforms 16 may be attached to a proximal end of the syringe body 14 to assist the user in traversing the plunger assembly 12 between a retracted position and a forward position. The safety syringe 10 may also comprise a detached needle assembly 18 which may be attached to the syringe body. One benefit of having the needle assembly 18 initially detached from the syringe body 14 and a selected needle assembly 18 attachable to the syringe body is that a medical professional may attach an appropriately sized needle 20 to the syringe body 14 depending on the particular mediation to be administered to the patient.

The safety syringe 10 is directed to a device and a method for maintaining sterility of fluidic medication during the entire process of withdrawing fluid medication from a medication container and injecting the fluidic medication to the patient. The safety syringe 10 accomplishes this by providing a barrier 22 between the environment which contains contaminated ambient air and a sterile variable fluid chamber 26.

In particular, the safety syringe 10 may be provided to a medical professional. The needle assembly 18 may initially be detached from the syringe body 14. Moreover, the plunger assembly 12 may be initially positioned in a retracted position when provided to the medical professional. As used herein, a retracted position of the plunger assembly is where a piston 28 of the plunger assembly 12 is closer to a proximal end of the syringe body 14 compared to a distal end portion 30 of the syringe body 14. When the safety syringe 10 is assembled by the manufacturer, the safety syringe 10 is also sterilized to kill or eliminate harmful or potentially harmful viruses, bacteria and other unwanted contaminants that may be on or in the safety syringe 10. More particularly, during the sterilization process, the inner surface of the variable fluid chamber 26 is sterilized. In particular, the inner surface of the variable fluid chamber 26 may be defined by a distal end 32 of the piston 28, an inner surface 34 of the syringe body 14 and a proximal surface 36 of the barrier 22.

In use, to administer a fluidic medication to a patient, the needle assembly 18 is attached to the distal end portion 30 of the syringe body 14. At or about the same time, the barrier 22 is punctured to allow fluidic medication to be drawn into the variable fluid chamber 26 and subsequently ejected out of the variable fluid chamber 26 and injected into the patient via the needle 20.

One of the many important aspects of the safety syringe 10 is that the inner surface of the variable fluid chamber 26 does not come into contact with the contaminated ambient air 24 during the process of attaching the needle assembly 18 to the syringe body 14. Before the needle assembly 18 is attached to the syringe body 14, the barrier 22 prevents contaminated ambient air 24 from entering into the variable fluid chamber 26. The barrier 22 is punctured to allow fluid and/or air to enter into or escape out of the variable fluid chamber 26 at or about the same time that the needle assembly 18 is attached to the syringe body 14. At such time, the needle assembly 18 then behaves as a cover after the barrier 22 is punctured such that ambient air does not enter into the variable fluid chamber 26 and possibly contaminate the variable fluid chamber 26 due to airborne viruses, bacteria or unwanted contaminants in the ambient air 24.

After the needle assembly 18 is attached to the syringe body 14, the fluidic medication may be withdrawn from a medication vial and be administered to the patient. In particular, the needle 20 of the syringe 10 may be inserted into a medication container or vial. At this time, the plunger assembly may be traversed toward the forward position. The forward position is defined where the piston 28 is closer to the distal end portion 30 of the syringe body 14 compared to a proximal end of the syringe body 14. As the plunger assembly 12 is traversed toward the forward position, sterilized air contained in the variable fluid chamber 26 is transferred into the medication container. Such transfer of sterilized air 38 increases the pressure within the medication container to assist in withdrawal of the fluidic medication therefrom. The medication container and safety syringe 10 may now be inverted such that the medication container is positioned over the safety syringe 10. A distal tip 40 of the needle 20 may be positioned within the fluidic medication contained in the medication container. Now the plunger assembly 12 may be traversed back toward the retracted position. Such retraction of the plunger assembly 12 traverses the fluidic medication contained in the medication container into the variable fluid chamber 26 of the safety syringe 10. As you will note, the fluidic medication in the variable fluid chamber 26 was not exposed to ambient air 24. The medical professional may remove the needle 20 from the medication container and remove any sterilized air 38 from within the variable fluid chamber by inverting the safety syringe 10, tapping on syringe body 14 to urge the sterilized air 38 toward the needle 20, and then slightly traversing the plunger assembly 12 toward the forward position to eject the sterilized air 38 and a negligible amount of the fluidic medication out of the variable fluid chamber 26 and the needle assembly 18. At this time, the medical professional may inject the patient with the fluidic medication contained in the variable fluid chamber 26.

Figure 3:
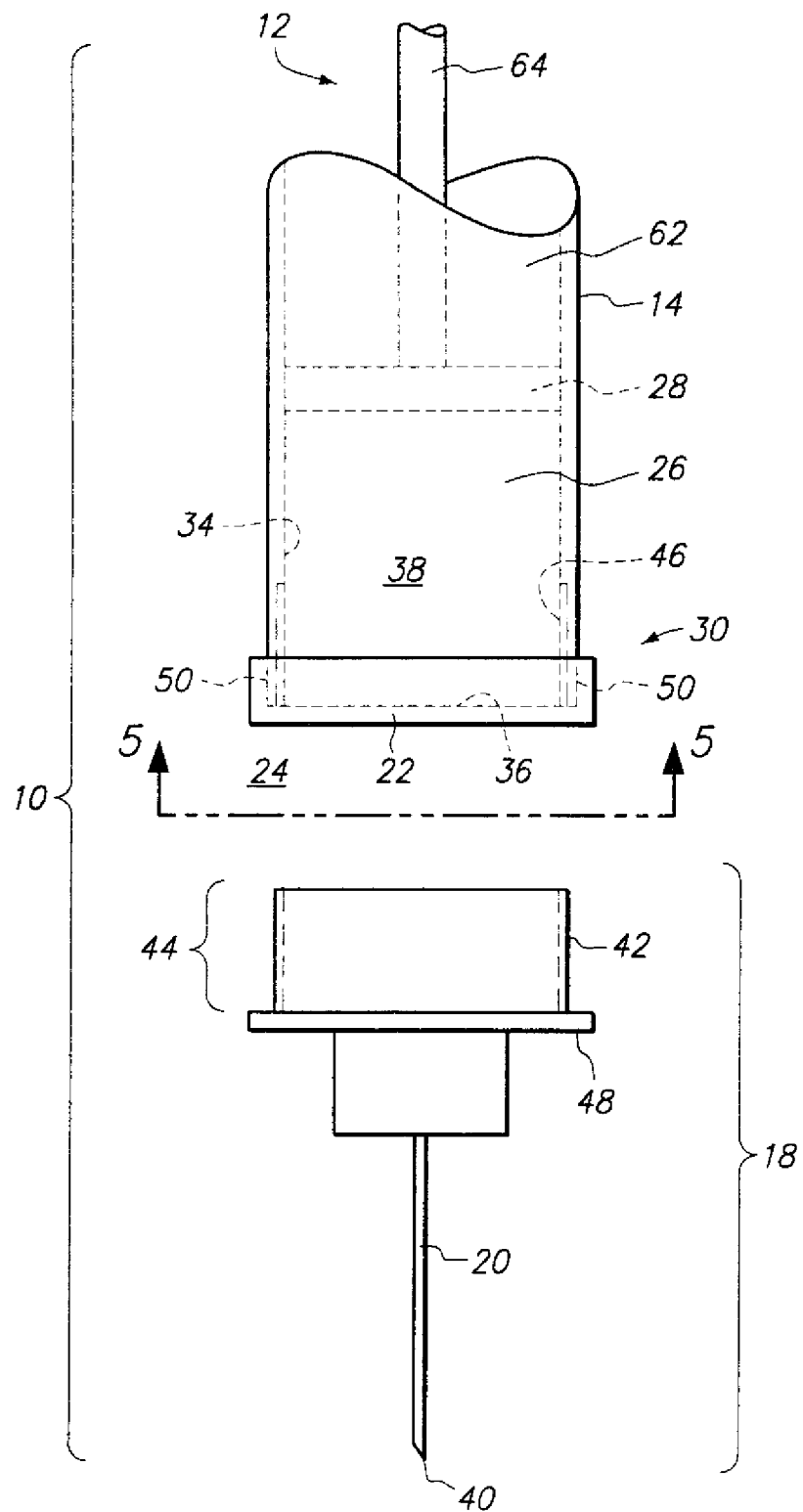
FIG. 3 is a front cross-sectional view of the safety syringe shown in FIG. 2.

In an aspect of the safety syringe 10, the needle assembly 18 may be attachable to the to the syringe body 14 in a plurality of different methods known in the art, discussed herein and those that are developed in the future. By way of example and not limitation, as shown in FIG. 3, the needle assembly 18 may have threads 42 disposed at a proximal end portion 44 of the needle assembly 18. Mating threads 46 may be formed at the distal end portion 30 of the syringe body 14. More particularly, the mating threads 46 may be formed on an inner surface 34 of the syringe body 14, whereas, the threads 42 of the needle assembly 18 may be formed on an outer surface of the proximal end portion 44 of the needle assembly 18. To attach the needle assembly 18 to the syringe body 14, the threads 42 may be threaded onto the mating threads 46. To lock the needle assembly 18 onto the syringe body 14, the needle assembly 18 may be formed with a stop flange 48. As the needle assembly 18 is threaded into the syringe body 14, the stop flange 48 may eventually contact the distal end portion 30 of the syringe body 14. The needle assembly 18 may then be cinched or tightened onto the syringe body 14 to insure frictional attachment between the needle assembly 18 and the syringe body 14. The above description of attaching the needle assembly 18 to the syringe body 14 is one embodiment of attaching the needle assembly 18 to the syringe body 14. The safety syringe 10 discussed herein should not be limited only to this embodiment but also contemplates any other methods and embodiments.

In an aspect of the safety syringe 10, various types of barriers 22 are contemplated. By way of example and not limitation, as shown in FIG. 3, the barrier 22 may be an air impermeable membrane disposed over the distal end portion 30 of the syringe body 14. The air impermeable membrane may be hermetically sealed about the outer periphery of the distal end portion 30 of the syringe body 14. Such seal is identified as reference numeral 50 in FIG. 3. The seal 50 may be formed via cold adhesive, hot adhesive, sonic welding as well as other methods known in the art or developed in the future. The air impermeable membrane prevents non-sterile air of the environment from entering into the variable fluid chamber 26 after the safety syringe 10 is removed from its packaging and prior to mounting of the needle assembly 18 onto the syringe body 14.

Figure 4:
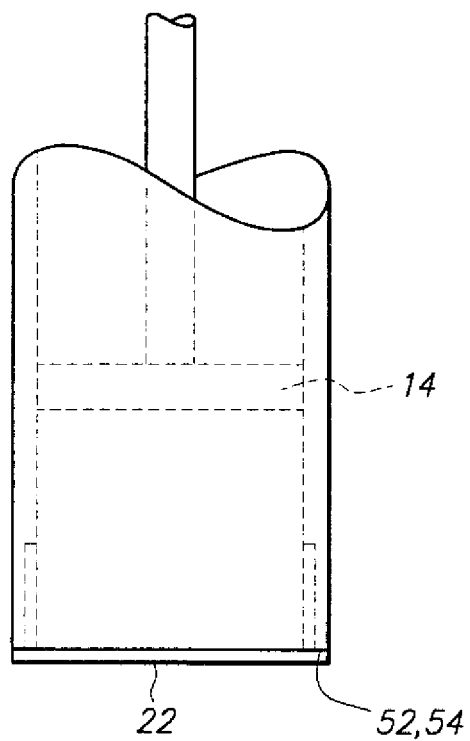
FIG. 4 is an alternate embodiment of attaching the barrier to the syringe body.

In another aspect of the safety syringe 10, as shown in FIG. 4, the barrier 22 may be attached to the distal end 52 of the syringe body 14. Such attachment may be made by cold adhesive, hot adhesive, sonic welding, as well as other methods that may be know in the art or developed in the future. The seal between the barrier 22 or air impermeable membrane and the distal end 52 of the syringe body 14 may be identified as reference numeral 54 in FIG. 4.

Figure 5:
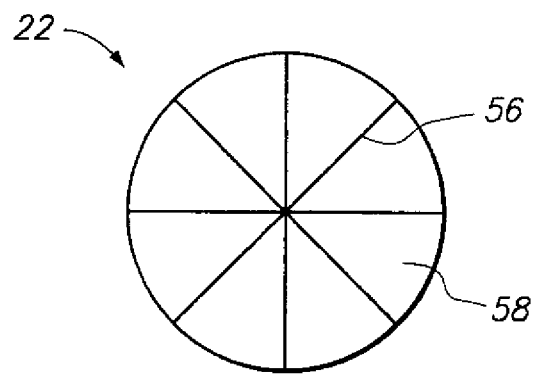
FIG. 5 is a bottom view of the barrier illustrating score lines forming eight pie-shaped pieces wherein the score lines are depressions formed in the barrier to control tearing, ripping or weakening of the barrier.
Figure 6:
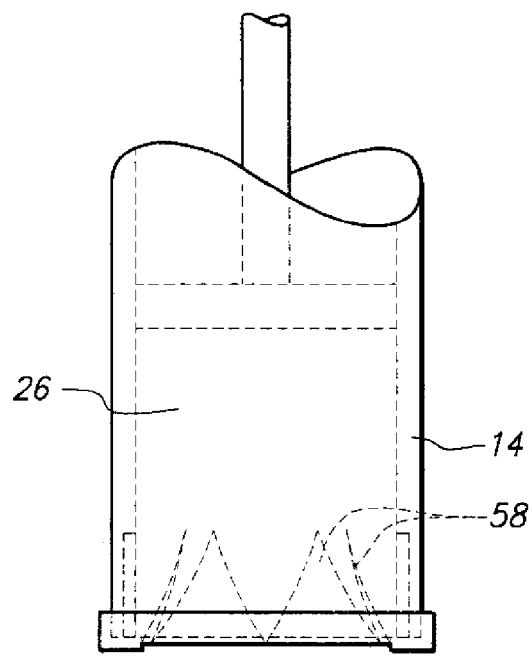
FIG. 6 illustrates the pie shaped pieces shown in FIGS. 2 and 5 when the barrier is punctured by the needle assembly.

In an aspect of the safety syringe 10, the puncturing of the barrier 22 may be controlled. In particular, as shown in FIG. 2 and FIG. 5, the puncturable barrier 22 may have a plurality of score lines 56. The score lines urge the puncturable barrier 22 to tear or weaken at the score lines 56 to permit fluid to pass through the barrier 22. The score lines 56 may be depressions formed on a proximal or distal side of the barrier 22. As shown in FIG. 6, when the needle assembly 18 (not shown in FIG. 6) is attached to the syringe body 14, pie-shaped pieces 58 of the harrier 22 are pushed into the variable fluid chamber 26. The pie shaped pieces 58 are disposed between the threads 42 of the needle assembly 18 and the mating threads 46 of the syringe body 14. Fluid (e.g., fluidic medication) may now pass into or out of the variable fluid chamber 26.

Figure 7:
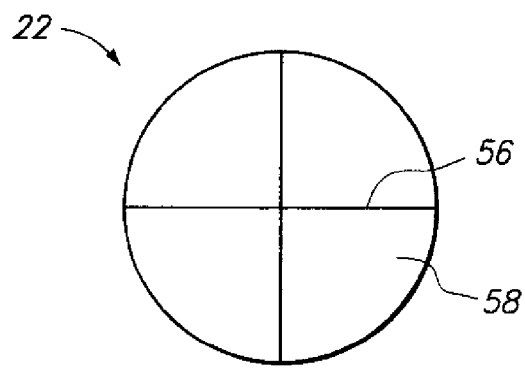
FIG. 7 is a bottom view of the barrier illustrating an alternate configuration of the score lines.
Figure 8:
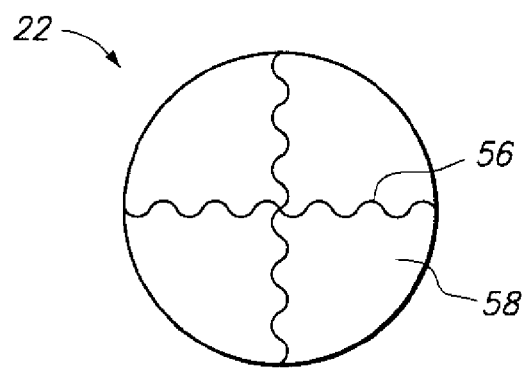
FIG. 8 is a bottom view of the barrier illustrating the score lines having a wavy configuration.

Although the score lines 56 as shown in FIG. 5 are formed as in a plurality of pie-shaped pieces 58, other configurations of the score lines 56 are contemplated. By way of example and not limitation, the score lines 56 may be formed on the puncturable barrier 22 as shown in FIG. 7. FIG. 8 shows an alternative embodiment of a different configuration of the score lines 56. As shown, each score line 56 may have a wavy pattern.

In an aspect of the barrier 22, the barrier 22 may be fabricated from an air impermeable material. By way of example and not limitation, the impermeable material may be plastic, paper, rubber, cloth, etc. The barrier 22 may be perforated but still be characterized as impermeable so long as a free flow of ambient air is not allowed to pass through the barrier 22 into the variable fluid chamber 26.

Figure 9:
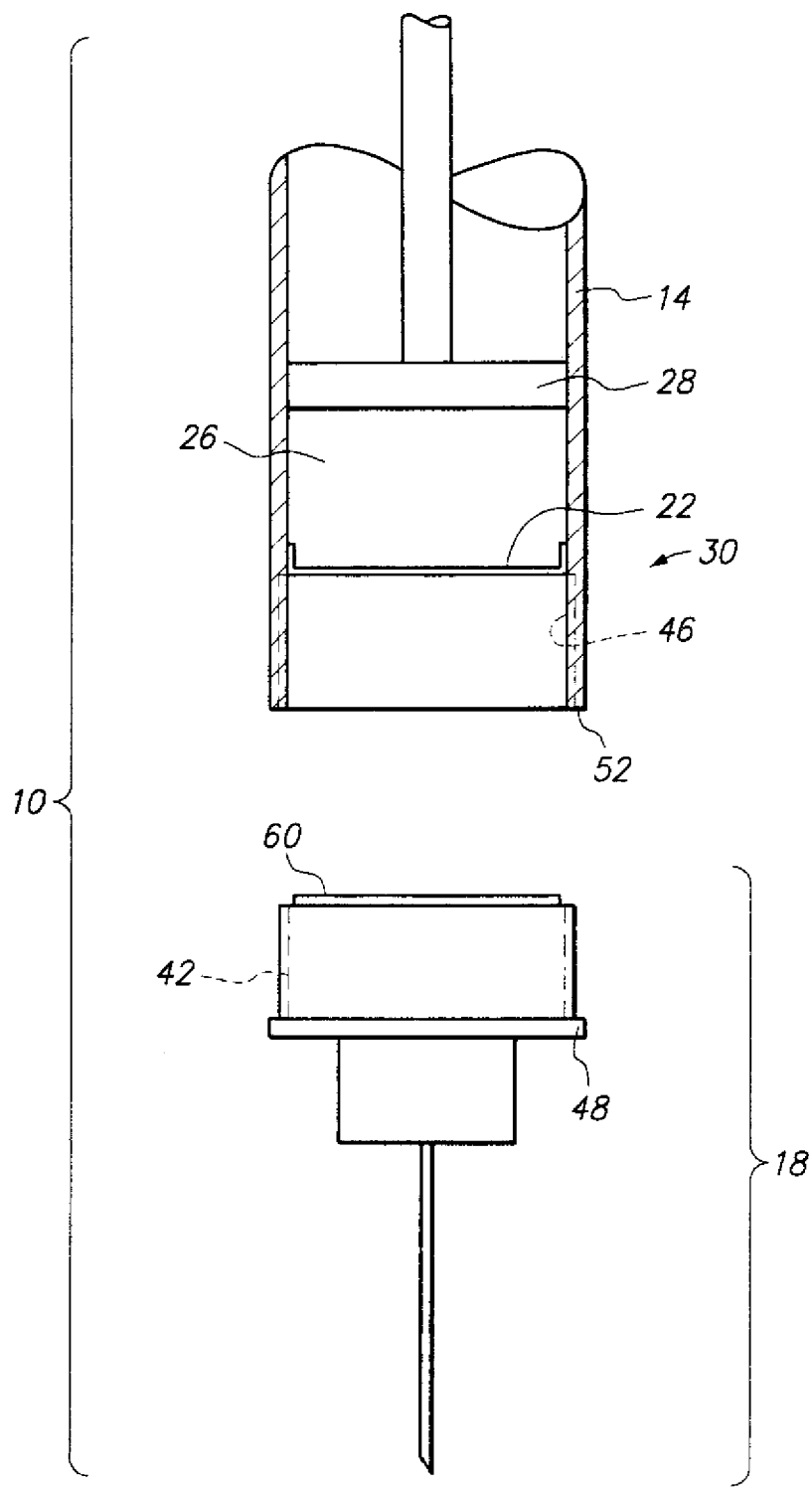
FIG. 9 is a front cross-sectional view of a safety syringe wherein the barrier is attached to an inner surface of the syringe body.

In another aspect of the safety syringe 10, as shown in FIG. 9, the barrier 22 may extend across the inner periphery of the syringe body 14 above the threads 42 of the mating threads 46 of the distal end portion 30 of the syringe body 14. To mount the needle assembly 18 to the syringe body 14, the threads 42 of the needle assembly 18 is threaded onto the mating threads 46. The needle assembly 18 is threaded into the syringe body 14 until the stop flange 48 contacts the distal end 52 of the syringe body 14. At or about the same time, a protrusion 60 of the needle assembly 18 may puncture the barrier 22. By way of example and not limitation, the protrusion 60 may at least slightly tear or weaken the barrier 22 to allow the fluidic medication to enter into or escape out of the variable fluid chamber 26. The barrier 22 may be characterized as punctured if the barrier 22 is torn or weakened so as to permit fluid to permeate through the barrier 22.

In an aspect of the safety syringe 10, the syringe 10 may be a sterilized vacuum assisted retractable safety syringe as discussed in U.S. application Ser. No. 11/511,668 ('668 application), filed Aug. 29, 2006, the entire content of which is incorporated herein by reference. The '688 application discusses how fluidic medication is injected into the patient in a sterile manner if the needle assembly is attached to the syringe body. In this regard, the discussion of the '668 application may be employed in the safety syringe 10 with detached needle assembly discussed herein after the detached needle assembly 18 is attached to the syringe body 14. Additionally, the safety syringe 10 may be a vacuum assisted retractable safety syringe as discussed in U.S. Pat. No. 6,413,236, filed Jun. 20, 2000 to Van Dyke, the entire content of which is incorporated herein by reference.

The safety syringe 10 may have a variable vacuum compartment 62 (see FIG. 3). When the plunger assembly 12 is in the retracted position, the variable vacuum compartment has a pressure equal to ambient pressure. As the plunger assembly 12 is traversed toward the forward position, the variable vacuum compartment 62 increases in volume but additional air molecules are not introduced into the variable vacuum compartment 62. The reason is that there is a seal between the piston 28 and the inner surface 34 of the syringe body 14 as well as a seal between a shaft 64 and proximal end of the syringe body 14. One benefit of the vacuum assisted retractable safety syringe 10 is that the inner surface of the variable fluid chamber 26 will not become contaminated by introduction of contaminants via the proximal end of the syringe body 14. Ambient air does not enter into the variable vacuum compartment 62 through the proximal end of the syringe body 14.

Although the variable vacuum compartment 62 and the variable fluid chamber 26 are separate compartments, during the process of injecting the patient with fluidic medication via the safety syringe 10, the variable fluid chamber 26 and the variable vacuum compartment 62 share a common surface, namely, the inner surface 34 of the syringe body. For example, the plunger assembly 12 is traversed between two positions, namely, the retracted position and the forward position. When the plunger assembly 12 is in the retracted position, the variable fluid chamber 26 typically has a larger volume compared to the variable vacuum compartment 62. When the plunger assembly 12 is traversed toward the forward position, the volume of the variable vacuum compartment 62 increases and the volume of the variable fluid chamber 26 decreases because the distal end 28 slides downward against the inner surface 34 of the syringe body 14. Accordingly, a portion of the inner surface 34 of the syringe body which used to define the variable fluid chamber 26 now at least partially defines the variable vacuum compartment 62.

If ambient air 24 were to enter into the variable vacuum compartment 62 via the proximal end of the syringe body 14, then contaminants contained in the ambient air 24 may be lodged onto the inner surface 34 of the syringe body. As the plunger assembly 12 is traversed between the retracted position and the forward position, the lodged contaminants on the inner surface 34 of the syringe body may eventually enter into the variable fluid chamber and thereby contaminate any fluidic medication drawn into the variable fluid chamber 26.

A benefit of the vacuum assisted retractable safety syringe is that the variable vacuum compartment 62 remains in a sterile state throughout the entire process of injecting the patient with fluidic medication because ambient air is not allowed into the variable vacuum compartment 62 via the proximal end of the syringe body 14.

Combining the vacuum assisted retractable safety syringe 10 with the barrier 22 provides a complete sterile environment in which the fluidic medication may be withdrawn into the variable fluid chamber 26 and subsequently injected into the patient without concern that the fluidic medication may become contaminated by exposure to the ambient air 24 or to contaminants that may have entered into the variable fluid chamber 26 via the proximal end of the syringe body 14.

In an aspect of the syringe 10, the detached needle assembly 18 may be attachable to the syringe body 14, as discussed in U.S. application Ser. No. 11/409,617, filed Apr. 24, 2006, the entire contents of which are expressly incorporated herein by reference. Additionally, the needle 20 of the needle assembly 18 may be retractable into the syringe body 14 as shown in U.S. application Ser. No. 11/409,617. Moreover, the barrier 22 may be attached to the distal end portion 30 of the syringe body 14 shown in FIGS. 1-5 of U.S. application Ser. No. 11/409,617.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A safety syringe for injecting a patient with fluidic medication in a sterile manner, the syringe comprising:
a plunger assembly having a piston and a shaft;
a syringe body, the syringe body having a proximal portion and a distal portion, the piston and shaft partially disposed within the syringe body, the piston being traversable between a retracted position and a forward position within the syringe body, the piston and syringe body defining a sterile variable fluid chamber, the sterile variable fluid chamber disposed on a distal side of the piston with sterile gas disposed therein;

a barrier attached to a distal portion of the syringe body and located distally from the variable fluid chamber, the barrier configured, before a needle is attached to the syringe, to prevent air transfer between an external environment and the sterile variable fluid chamber and to maintain sterility of the variable fluid chamber; and a detached needle assembly, having a needle end and a syringe end without a needle, attachable at the syringe end to the distal portion of the syringe body and operative when attached at the syringe end to the distal portion of the syringe body to puncture the barrier to allow fluidic medication to flow into or out of the sterile variable fluid chamber through the needle assembly.

2. The syringe of claim 1 wherein the barrier is configured to be torn when it is punctured.

3. The syringe of claim 1 wherein the barrier is air impermeable and hermetically sealed to the distal portion of the syringe body.

4. The syringe of claim 1 wherein the barrier is weakened in a pattern and operative to rupture in accordance with the pattern upon puncturing by attachment of the detached needle assembly to the syringe body.

5. The syringe of claim 4 wherein the pattern is a plurality of score lines or perforations.

6. The syringe of claim 4 wherein the pattern has a configuration of a pie cut into a plurality of pieces.

7. The syringe of claim 4, wherein the pattern comprises wavy lines.

8. The syringe of claim 1 wherein the barrier is attached to the syringe body closer to the distal portion than to the proximal portion of the syringe body.

9. The syringe of claim 1, further comprising:

first threads disposed on an inner surface of the syringe body; and second threads disposed on an outer surface of the needle assembly, the second threads configured to mate with the first threads.

10. The syringe of claim 9, wherein the needle assembly is configured to puncture the barrier when the second threads on the needle assembly are threaded onto the first threads.

11. The syringe of claim 1, wherein the barrier is disposed within the syringe body.

12. The syringe of claim 1, wherein the barrier is disposed at a distal end of the syringe body.

13. A method of injecting a fluid in a person, the method comprising the steps of:

receiving a syringe body with a barrier attached to a distal portion of the syringe body, the barrier configured to prevent free flow of air transfer between an environment and a sterile variable fluid chamber of the syringe body prior to attachment of a needle assembly to the syringe body, the sterile variable fluid chamber disposed on a distal side of a piston, the piston being disposed in a retracted position with the syringe body and sterile gas disposed within the sterile variable fluid chamber;

attaching a needle assembly to the distal portion of the syringe body, the needle assembly having a needle end and a syringe end without a needle, the syringe end of the needle assembly configured to puncture the barrier when the needle assembly is attached to the syringe body in order to allow fluidic medication to flow into or out of the sterile variable fluid chamber through the needle assembly;

puncturing the barrier with the syringe end of the needle assembly, to permit flow of fluid through the punctured barrier;

inserting a needle of the needle assembly into a container containing fluidic medication;

traversing a piston toward the distal end portion of the syringe body to transfer the sterile gas within the sterile variable fluid chamber into the container to pressurize the container and assist in subsequent withdrawal of the fluidic medication contained in the container;

positioning an opening of the needle within the fluidic medication in the container;

transferring the fluid in the container into the sterile variable fluid chamber; and injecting the person with the fluid in the sterile variable fluid chamber.

14. The method of claim 13, wherein attaching the needle assembly to the distal portion of the syringe body further comprises threading the needle assembly onto matching threads disposed on the body of the syringe.

15. The method of claim 14, wherein threading the needle assembly onto the matching threads causes the needle assembly to puncture the barrier.

16. The method of claim 13, wherein the barrier is disposed within the syringe body.

17. The method of claim 13, wherein the barrier is disposed at a distal end of the syringe body.

* * * * *